United States Patent [19]

Arai et al.

[11] 4,372,947
[45] Feb. 8, 1983

[54] ANTIBIOTIC SAFRAMYCIN S AND PROCESS FOR PRODUCING THE SAME

[75] Inventors: Tadashi Arai, 6-50-6, Nogata, Nakano-ku, Tokyo, Japan; Katsuhiro Takahashi, Tokyo, Japan; Kimiko Ishiguro, Kamagaya, Japan; Koji Yokoyama, Chiba, Japan

[73] Assignee: Tadashi Arai, Tokyo, Japan

[21] Appl. No.: 189,756

[22] Filed: Sep. 23, 1980

[30] Foreign Application Priority Data

Mar. 26, 1980 [JP] Japan ................................. 55-38403

[51] Int. Cl.$^3$ .................. A61K 35/00; C07D 521/00; C12P 1/06
[52] U.S. Cl. .................................. 424/121; 544/342; 435/169
[58] Field of Search ........................ 424/121; 435/169; 544/342

[56] References Cited

U.S. PATENT DOCUMENTS 4,081,531  3/1978  Arai ..................................... 424/121
4,127,446  11/1978  Arai ..................................... 424/121
4,248,863  2/1981  Arai ..................................... 424/122

OTHER PUBLICATIONS

Chemical Abstracts 90:166572w (1979).

Primary Examiner—Jerome D. Goldberg
Attorney, Agent, or Firm—Frishauf, Holtz, Goodman & Woodward

[57] ABSTRACT

Antibiotic substance named saframycin S having antibacterial activities and produced by decyanating antibiotic saframycin A or cultivating *Streptomyces lavendulae* strain No. 314 and recovering saframycin S from a cultured broth.

2 Claims, 3 Drawing Figures

FIG. 2

FIG. 3

ANTIBIOTIC SAFRAMYCIN S AND PROCESS FOR PRODUCING THE SAME

This invention relates to a new antibiotic substance saframycin S and a process for producing the same.

More particularly, it is concerned with an anti-biotic substance named saframycin S having antibacterial activities mainly against gram-positive bacteria and activity against transplantable tumors. It is also concerned with a process for the production of antibiotic substance saframycin S, which comprises decyanating antibiotic saframycin A or cultivating *Streptomyces lavendulae* strain No. 314 and recovering saframycin S from a cultured broth.

Heretofore, isolation of about 3,000 different types of antibiotic substances has been reported and it has become difficult in the art to find a new antibiotic substance.

The present inventors have made minute studies on the products obtained by cultivating actinomycetes which have been already known to produce some antibiotic substances and have been ready to be neglected without further studies. As a result, it has been found that some of the actinomycetes capable of producting known antibiotics can also produce a small quantity of new antibiotics different from known antibiotics on chemical properties and biological activities. We have proposed to call collectively these antibiotics "satellite antibiotics". As an example of such an antibiotic, we have isolated an antibiotic saframycin group from a cultured broth of actinomycetes producing known streptothricin, *Streptomyces lavendulae* strain No. 314. Saframycins A, B, C, D and E have been isolated, identified and reported. Saframycin A has potent biological activity and shows a strong antitumor effect (Japanese Patent Lay Open No. 44098/1979). Chemical structures of saframycins A, B and C are presumably as shown below. All of them have a novel dimerized heterocyclic quinone as a basic skeleton.

|  | $R_1$ | $R_2$ |
|---|---|---|
| Saframycin A | H | CN |
| B | H | H |
| C | OCH$_3$ | H |

Saframycin A has one nitrile group at the $C_{21}$-position and, as a result of investigation on mechanism of its pharmacological action, this nitrile group is supposed to have an important meaning to bind the antibiotic to DNA in tumor cells. It was ascertained that saframycin A is activated on reduction in vivo, whereby the nitrile group is eliminated as nitrile ion. It is supposed that antibiotic saframycins are biosynthesized from tyrosine and five varieties of the saframycins are naturally biosynthesized from the same intermediate.

By the above two reasons, the decyanated saframycin A is considered to be a basic substance in the biosynthesis of the antibiotic saframycin group. This invention relates to such a decyanated saframycin A, which is hereinafter referred to as saframycin S.

It is, accordingly, a primary object of this invention to provide a new antibiotic substance saframycin S which shows valuable biological activities.

Another object of this invention is to provide a process for the production of this new antibiotic substance.

These and other objects and advantages of this invention will be apparent from the description as stated below.

Saframycin S can be prepared by decyanating saframycin A.

Saframycin A used as the starting material in the present invention may be obtained by cultivating *Streptomyces lavendulae* strain No. 314 according to the method described in the above Japanese Patent Lay Open No. 44098/1979. The strain has been deposited under the accession No. 3218 in Technical Research Institute of Microbial Industry, Agency of Industrial Science & Technology, Ministry of International Trade and Industry, Japan.

Saframycin A is subjected to acid-decomposition by heating with a diluted mineral acid or glacial acetic acid under reflux. The nitrile group is eliminated and hydrogen cyanide gas produced is collected in an alkaline solution to obtain denitrilated saframycin A, i.e., saframycin S. After completion of the reaction, the reaction mixture is neutralized and extracted with a solvent which is water-immiscible and capable of dissolving saframycin S. The extract is concentrated under reduced pressure and the residue is purified by column chromatography with absorbent such as silica gel to obtain saframycin S as dark yellow powder.

Figure 1:
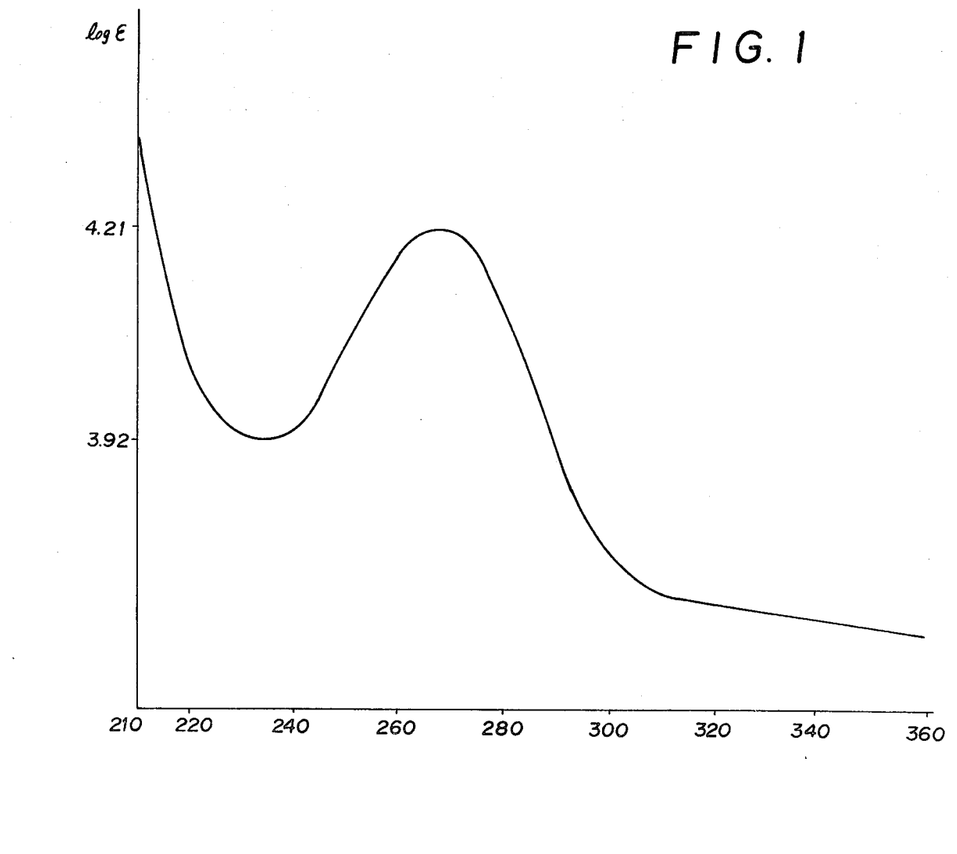
Figure 2:
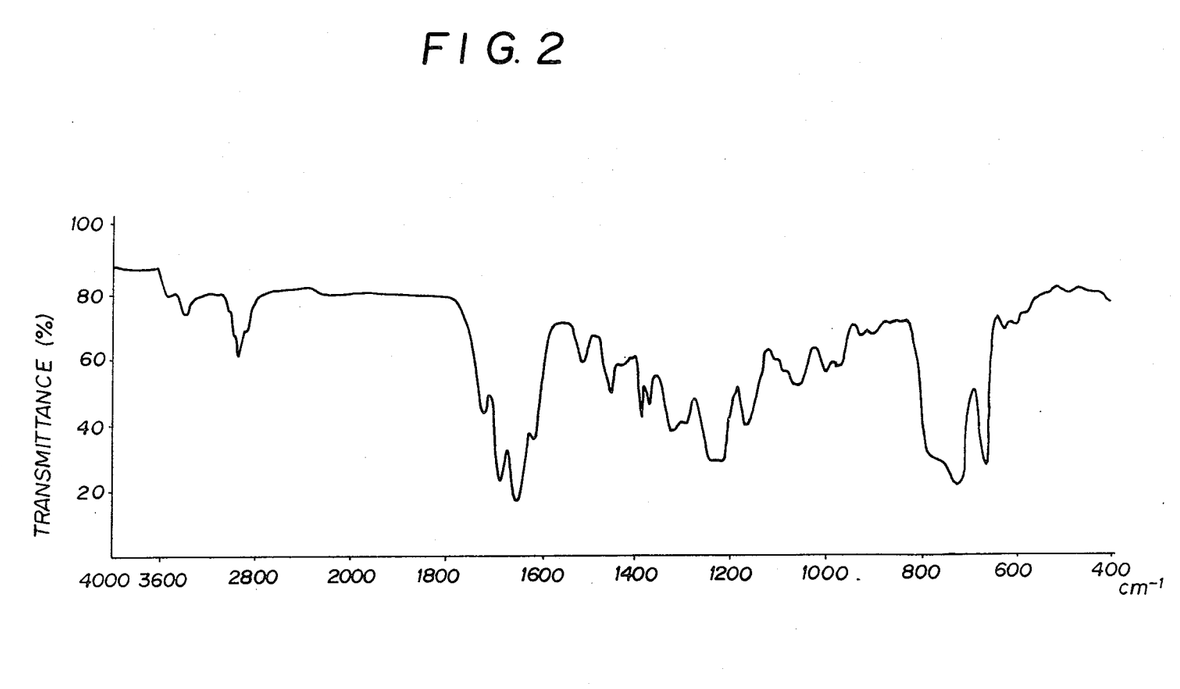
Figure 3:
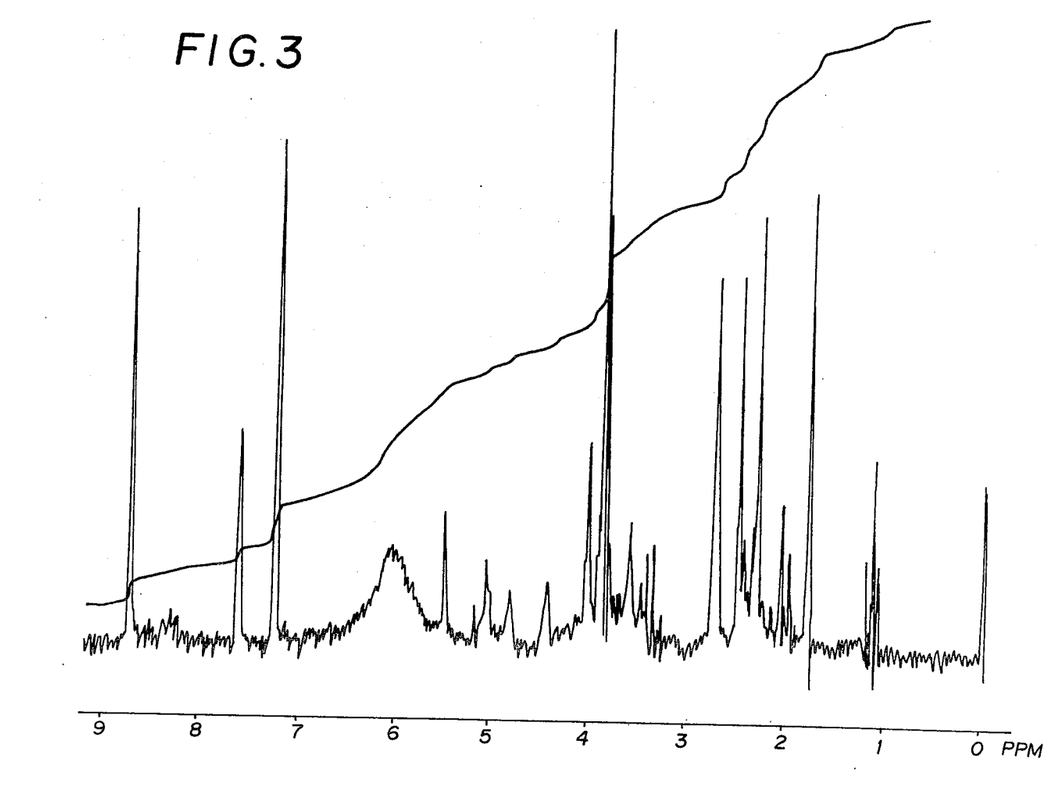

Saframycin S has the following characteristics:
(1) Color and appearance:
   dark yellow powder
(2) Melting point:
   107°–115° C.
(3) Specific rotation:
   $[\alpha]_D^{25} = +32.5$ (0.5 MeOH)
(4) Elementary analysis:
   C: 61.09%, H: 6.67%, N: 7.49%
   C: 61.45% H: 6.18%, N: 7.48%
(5) Molecular weight
   553
(6) Empirical formula
   $C_{28}H_{30}N_3O_8{}^+ \cdot OH^-$
(7) Ultraviolet absorption spectrum as shown FIG. 1:
   UV $\lambda_{max}^{MeOH}$ nm (log $\epsilon$): 268 (4.21)
   UV $\lambda_{min}^{MeOH}$ nm (log $\epsilon$): 234 (3.92)
(8) Infrared absorption spectrum as shown in FIG. 2:
   IR $\nu_{max}^{CHCl_3}$ cm$^{-1}$: 3400, 1720, 1680, 1650
(9) NMR spectrum ($C_6H_5N$) as shown in FIG. 3 (measured with 100 MHz in pyridine and with TMS as an internal standard):
   $\delta$(ppm): 1.88 (3H, s), 2.30 (3H, s), 2.48 (3H, s), 2.72 (3H, s), 3.82 (3H, s), 3.85 (3H, s), 5.46 (1H, s).
(10) Chemical structure:
   Supposed to have the following structure of an immonium type or $\alpha$-carbinol amine type.

Saframycin S can be converted to saframycin A with about 50% yield by treating it with sodium cyanide in a weakly acidic or neutral aqueous solution at room temperature for 40-60 minutes (Example 4).

Alternatively, saframycin S can be prepared by cultivating Streptomyces lavendulae strain No. 314 and recovering saframycin S from a cultured broth.

Streptomyces lavendulae strain No. 314 in this invention was isolated from a soil sample collected at Kyoto and belongs to the genus Streptomyces. This strain has been deposited under the accession No. 3218 in Technical Research Institute of Microbial Industry, Agency of Industrial Science & Technology, Ministry of International Trade and Industry, Japan and also as NRRL-11002 in the Northern Regional Research Laboratory, Northern Central Region, Agricultural Research Service, United States Department of Agriculture, at Peoria, Illinois, U.S.A.

Observation of aerial mycelium and spores of Streptomyces lavendulae strain No. 314 was effected by cultivating the strain on the media according to the methods of the International Streptomyces Project (ISP) (Shirling. E. B. & D. Gottlieb; International J. Systematic Bacteriol. 16, 313-340, 1966); namely, by cultivating on agar plate of yeast-starch-agar medium, inorganic salts-starch-agar medium and maltose-containing basal medium for carbon source utilization pattern (Pridham-Gottleib's agar medium) at 27° C. for 1-2 weeks. Also, colors of mycelium with mature spores, vegetative mycelium and others were determined according to the color chip number as suggested in "Descriptive Color Name Dictionary", Container's Corporation of America, 1950 and "Color Harmony Manual", Container's Corporation of America, 1958.

The strain No. 314 develops wave-shaped flexious long-branched aerial mycelium in a diameter of about 0.6-1.0μ with many cylindrical spores. Spores are 0.6-1.0μ×0.8-2.0μ in size. According to the standard in ISP, the strain having the above morphological characteristics is said to belong to the Section Rectiflexibiles. However, the aerial hyphae with loops or incopmplete or elongated spirals which are in coils of 1-2 turns, can be observed on some instances. Therefore, the strain No. 314 has been morphologically determined to belong to the Section Retinaculiaperti. When spore surface on these media are observed under electron microscope, the spore of the strain has been found to have a smooth surface. The strain No. 314 has main characteristics in that the aerial hyphae are morphologically of the Section Retinaculiaperti, color of the aerial hyphae with mature spores is rose to lavender on various media, color of the vegetative mycelium is sometimes blue to bluish brown on a synthetic medium and production of melanin pigment is positive. Then, searching the strains of the genus Streptomyces which are described in "The Actinomycetes", S. A. Waksman, Vol. 2, 1959 and "Bergey's Determinative Bacteriology", 8th Ed., 1974, it was shown that the strain has close resemblance to *Streptomyces lavendulae*. The strain No. 314 is inoculated to a conventional medium for producing an antibiotic substance and shaken culture is effected at 27° C. for a cultivation period of 18 to 72 hours to produce a culture filtrate having a high activity against *coliform bacilli*. The filtrate thus obtained is treated with active charcoal under alkaline condition, eluted with acidic acetone or adsorbed on a weak cation exchange resin, for example, Amberite IRC-50 (trade name, available from Rohm & Haas Co., U.S.A.) and subjected to desorption with 0.1 N hydrochloric acid to afford an antibacterial substance against *coliform bacilli*. Then, the substance thus obtained is purified by chromatography over, for example, Amberite CG-50 (trade name, available from Rohm & Haas Co.) and crystallized in the form of its Reinecke's salt or picrate, whereupon this substance is identified as streptothricin.

Further, comparison of cultural and physiological characteristics was made by the use of *Streptomyces lavendulae* IFM 1031, which is a streptothricin-producing strain, *Streptomyces racemochromogenes* IFM 1081, which is considered to be identical with *Streptomyces lavendulae* and capable of producing streptothricin, and the present strain for final identification. The results are summarized in Tables 1, 2 and 3. More specifically, the strain No. 314 has been identical with *Streptomyces lavendulae* in every characteristic property which is presently applied for identification of the strain in the genus Streptomyces, though minor differences are observed in some respects, for example, utilization of L-arabinose and the like, and thus the strain has been identified as *Streptomyces lavendulae*. Also, *Streptomyces racemochromogenes* can produce streptothricin, but this strain is apparently different from the strain No. 314 which is *Streptomyces lavendulae* from the above-mentioned comparison results.

TABLE 1

| | Comparison of Streptomyces strain No. 314 with known strains | | |
|---|---|---|---|
| Medium | Strain No. 314 | Streptomyces lavendulae IFM 1031 | Streptomyces racemo-chromogenes IFM 1081 |
| Sucrose- | AM abundant, white to | AM abundant, ivory (2 db) | AM abundant, ivory (2 db) |

TABLE 1-continued
Comparison of Streptomyces strain No. 314 with known strains

| Medium | Strain No. 314 | *Streptomyces lavendulae* IFM 1031 | *Streptomyces racemochromogenes* IFM 1081 |
|---|---|---|---|
| nitrate agar (Czapek's medium) | ivory (2 db) VM spreading growth, colorless to faint olive (1½ ie) DP none, or faint brown | to gray (3 dc) VM spreading growth, colorless to faint brown DP faint brown | to gray (5 dc) VM faint brown to purple brown (11 nl) DP faint brown |
| Glucose-asparagine agar (Krainsky) | AM abundant, pink to lavender (5 ge) VM spreading growth, colorless to faint olive (1½ ie) DP none, or faint brown | AM abundant, pink to lavender (5 ge) VM spreading growth, bluish blue (10 pn) DP none, or faint brown | AM abundant, pink to lavender (5 ge) VM spreading growth, brown to blue (10 pn) DP none, or faint brown |
| Glycerol-asparagine agar (ISP) | AM moderate, faint brownish gray to silver gray (3 fe) VM spreading growth, colorless, sometimes blue colonies DP none | AM small amount, silver gray (3 fe) VM olive to bluish blue (1½ pn) DP faint brown | AM moderate, silver gray (3 fe) VM dark olive (1½ pn) DP faint olive brown |
| Calcium-malate agar | AM moderate, powdery, pink (3 ba) VM spreading growth, dark olive (1½ nl) DP none, or faint bluish brown | AM none VM spreading growth, bluish brown (3 pn) DP faint brown | AM none VM spreading growth, bluish brown (3 pn) DP faint olive brown |
| Inorganic salts-starch agar (ISP) | AM abundant, yellowish gray (3 dc) VM colorless DP none | AM abundant, gray (3 dc) VM colorless to dark olive (2 po) DP none | AM abundant, gray (3 dc), bluish gray (2 po) VM dark olive (2 po) DP faint olive brown |
| Nutrient agar | AM none VM spreading growth, glistening surface, camel (3 ie) DP faint brown | AM none VM spreading growth, glistening surface, camel (3 ie) DP faint brown | AM none VM spreading growth, glistening surface, camel (3 ie) DP faint brown |
| Yeast extract-salt extract agar (ISP) | AM abundant, spots with pink to white (5 ge) VM folded, colorless to faint brown DP dark brown (4 pi) | AM abundant, pink (5 ge) VM spreading growth, colorless to faint brown DP dark brown (4 pi) | AM abundant, pink (5 ge) VM folded, faint brown DP dark brown (4 pi) |
| Oatmeal agar (ISP) | AM moderate, white to pink (4 ca) VM colorless DP none | AM moderate, pink to lavender (5 ec) VM blue (15 ni) DP none, or bluish brown | AM moderate, pink (3 ca) VM bluish brown (15 ni) DP none, or faint brown |
| Egg medium | AM none VM much folded, chocolate (4 pl) DP chocolate brown | AM poor, white VM much folded, chocolate (4 pl) DP chocolate brown | AM poor, to none VM much folded, chocolate (4 pl) DP chocolate |
| Tyrosine synthetic medium | AM abundant, pink (7 ge) VM spreading growth, mustard brown (2 ni) DP none, or faint brown | AM abundant, pink (7 ge) VM spreading growth mustard brown (2 ni) DP none, or faint brown | AM abundant, pink (7 ge) VM spreading growth mustard brown (2 ni) DP none, or faint brown |

AM: aerial mycelium
VM: vegetative mycelium
DP: water-soluble pigment (color of medium)

TABLE 2
Comparison of physiological properties of Streptomyces strain No. 314 with known strains

| Physiological property | Strain No. 314 | *Streptomyces lavendulae* IFM 1031 | *Streptomyces racemochromogenes* IFM 1081 |
|---|---|---|---|
| Nitrate reduction (14 days) | + | + | + |
| Liquefaction of gelatin (18° C., 21 days) | + | + | + |
| Soluble pigment | brown | brown | brown |
| Hydrolysis of cellulose (21 days) | − | − | − |
| Litmus milk Coagulation | ++ | ++ | ++ |
| Peptonization | ++ | ++ | ++ |
| pH | 8.0 | 7.8 | 7.8 |

TABLE 2-continued

Comparison of physiological properties of Streptomyces strain No. 314 with known strains

| Physiological property | Strain No. 314 | Streptomyces lavendulae IFM 1031 | Streptomyces racemochromogenes IFM 1081 |
| --- | --- | --- | --- |
| Melanin fomation | + | + | + |

TABLE 3

Comparison of carbon source utilization pattern of Streptomyces lavendulae strain No. 314 with known strains

| Carbon source | Strain No. 314 | Streptomyces lavendulae IFM 1031 | Streptomyces racemochromogenes IFM 1081 |
| --- | --- | --- | --- |
| D-xylose* | − | ± | − |
| L-arabinose* | + | − | − |
| L-rhamnose* | − | − | − |
| D-glucose* | + | + | + |
| D-fructose* | ± | ± | − |
| sucrose* | + | + | + |
| lactose | − | − | − |
| maltose | + | + | + |
| raffinose* | − | − | − |
| mannitol* | − | − | − |
| i-inositol* | − | − | − |
| sodium acetate | + | + | + |
| sodium citrate | + | + | + |
| sodium succinate | + | + | + |
| Control | − | − | − |

*carbon source described in ISP.

Saframycin S which can be produced according to this invention have not previously been isolated from a cultured broth of the aforesaid well-known microorganisms belonging to *Streptomyces lavendulae.*

According to the process of this invention, saframycin S can be produced by cultivation of *Streptomyces lavendulae* strain No. 314.

Cultivation may be principally conducted according to conventional cultivation procedures of a microorganism, but it is usually favourable to effect submerged culture in a liquid medium. As the medium which may be employed in this invention, there may be any media containing nutrients which the strain No. 314 of the genus Streptomyces may utilize. More specifically, synthetic, semisynthetic or natural media may be used and, as examples of medium components, there may be mentioned a carbon source, such as glucose, maltose, fructose, xylose, starch, glycerol and the like; a nitrogen source, such as meat extract, peptone, gluten meal, cotton seed oil, soybean meal, corn steep liquor, dry yeast, yeast extract, ammonium sulfate, ammonium chloride, urea and other organic or inorganic nitrogen sources. Carbonates, phosphates or other salts of metals may be additionally incorporated into a medium. In case where an exceeding foaming is observed during cultivation, it is convenient to add to a medium an anti-foaming agent, such as a vegetable oil, e.g., soybean oil; silicone oil; polyoxyalkylene type agents; mineral oils and the like.

Cultivation temperature is usually within a range of about 27°–30° C. As a volume of the medium is increased, it is suitable to effect seed cultures and then inoculate the seed cultures to a fermentation medium. Cultivation time is usually from about 18 hours to about 24 hours.

The aforesaid culture conditions may be selected for optimum and applied depending upon the microorganism to be used for production of the present antibiotics.

The antibiotic substances thus accumulated in a cultured broth are usually included within mycelia and culture liquid and extracted from the mycelia collected by centrifugation or filtration and the filtrate thus recovered. More specifically, the present antibiotic substance may be isolated, recovered and purified by conventional procedures commonly employed for the production of a natural product, for instance, those utilizing solubility and solubility difference in suitable solvents, separability and difference in a separating rate from a solution, difference in adsorption and affinity on various adsorbents, difference in distribution between two liquid phases and the like. These procedures may be applied, if desired, alone or in optional combination therewith or repeatedly. A representative procedure will be set forth below.

After completion of the cultivation, the cultured broth is filtered to separate mycelia from the filtrate. The filtrate is adjusted to pH 8.0 with 10 N sodium hydroxide. The filtrate may be previously concentrated to ½–⅓ volume for better extraction efficiency with a solvent. In the solvent extraction as noted above, basic, water-soluble antibiotics, for example, streptothricin simultaneously produced by the strain No. 314 are left in the filtrate, while saframycin complex and the like are extracted into the solvent phase. The solvent phase is concentrated to dryness under reduced pressure, the concentrate is dissolved in a small amount of ethyl acetate, the solution is shaken with aqueous sodium carbonate and separated, whereupon acidic substances are transferred into an aqueous phase. The solvent phase is extracted with 1 N hydrochloric acid, adjusted to pH 8–9 with aqueous ammonia and extracted with chloroform. This step is repeated several times and the solvent phase is concentrated to dryness under reduced pressure to give a reddish brown, crude basic component containing saframycin complex. The crude basic component is dissolved in a small amount of ethyl acetate, the solution is washed several times with a small amount of water and shaken with 1 N hydrochloric acid, whereupon the antibiotic substances are transferred into an aqueous layer. The aqueous layer is adjusted to pH 8.0 carefully and extracted with dichloromethane. The dichloromethane layer is separated, dried over anhydrous sodium sulfate and the solvent is distilled off to obtain dark red solid, which contains all of saframycins A, B, C, D, E and S. The solid is chromatographed over silica gel column, which is then developed successively with a mixture of benzene and ethyl acetate (10:1), (4:1) and (2:1). Saframycin S is eluted with an eluent of the mixture (2:1) and further purified by preparative thin layer chromatography. Saframycin S is obtained as a dark yellow powder. Saframycin S was subjected to thin layer chromatography over silica gel, which was developed successively with benzene:acetone (1:1), benzene:ethyl acetate (1:3) and chloroform:ethyl acetate (1:1) and gave yellow spots at the position of Rf values of 0.45, 0.25 and 0.16, respectively. Identification and quantitative determination of saframycin S was conducted by measuring the position and area of the yellow spots on scanning profile with 270 nm.

We found that among saframycins A-E, saframycin A has the highest biological activity, and is effective in inhibiting the growth of various microorganisms at low concentrations, as well as for leukemia (L1210 and P388), melanoma B16, Ehrlich's ascites tumor, and S-180 solid cancer of mouse which are used internationally as a tool to evaluate anti-cancer agents. We also found that it was effective in inhibiting the growth of gastric cancer of man heterotransplanted to the nude mouse.

The studies of mechanism of action on saframycin A revealed that this substance specifically reacted with DNA of transplantable cancer cells to inhibit their template activity, and thereby prevented synthesis of ribosomal RNA and messenger RNA. However, Saframycin A did not inhibit RNA synthesis in in vitro reaction mixture containing *Escherichia coli* RNA polymerase, calf thymus DNA and appropriate RNA precursor.

Further study on the above point clarified that saframycin needed to have been reduced in advance for reaction with DNA, and addition of dithiothreitol (DTT) and other reducing agent to RNA synthesizing system in vitro would cause saframycin A reaction with DNA to proceed as in vivo, and that RNA synthesis inhibition equivalent to in vivo effect was observed.

Saframycin A is unique in that it has nitrile group at C-21 position. When saframycin A is reduced and activated, the cyano group is eliminated from the molecule, and saframycin A reacts with DNA as decyanosaframycin A. The inventors of this invention first studied the method of chemically preparing decyanated decyanosaframycin A, saframycin S, from saframycin A, and succeeded in discovering the method.

As anticipated, saframycin S presented still more powerful biological activities in every point than saframycin A.

On the other hand, we reviewed various conditions for culture in order to raise potencies of saframycin A culture solution, and discovered that if NaCn or KCN is added to culture solution when the potency reached its maximum, the potency radically increased. This suggested that the precursor for saframycin A existed in a great amount in the culture solution and that these are converted to saframycin A by the addition of cyano ions. We estimated one of these precursors as probably saframycin S. Thus, it led us to the study of extraction and purifying of the precursors for saframycin A from the culture solution, isolation of effective substance, and identifying the same with saframycin S, which completed the present invention.

As mentioned above, chemical structure of saframycin S may be in both immonium type and α-carbinol amine type. However, it is now considered that the immonium type compound is predominant. Saframycin S, due to a new reactive hydroxy group at the $C_{21}$-position, is very useful as a basic compound from which more excellent derivatives can be synthesized.

Saframycin S is a basic antibiotic substance and thus capable of forming the corresponding acid addition salts, which are intended to fall under the scope of this invention. Typical examples of such acid addition salts are those formed with hydrochloric acid, sulfuric acid, phosphoric acid, stearic acid, propionic acid, tartaric acid, maleic acid and the like. As can be expected, the salts of this sort can exert the same antibiotic activity and activity against transplantable tumors as the free antibiotic substance do, but there may be usually seen differences in activity and solubility property between them.

Antibacterial spectra of saframycin S are shown in Table 4 comparing with that of saframycin A.

Medium and culture condition:

1% glucose nutrient agar (3% glycerol nutrient agar for acid-fast bacteria, blood agar for *Streptococcus pyogenes* and *Brucella abortus*), 37° C., 24 or 48 hours.

Sabouraud dextrose agar for fungi, 27° C., 48 hours.

TABLE 4

| Antimicrobial spectra of saframycin S | | |
|---|---|---|
| | MIC (μg/ml) | |
| Test organisms | Saframycin S | Saframycin A |
| Staphylococcus aureus 209P | 0.01 | 0.05 |
| Staphylococcus aureus Smith | 0.001 | 0.025 |
| Staphylococcus albus | 0.001 | 0.006 |
| Staphylococcus citreus | 0.001 | 0.006 |
| Streptococcus faecalis | 1.56 | 1.56 |
| Streptococcus pyogenes Cook | 0.05 | 1.56 |
| Streptococcus pyogenes 090R | 0.05 | 3.0 |
| Staphylococcus salivarius | 25.0 | 50.0 |
| Salina lutea | 0.006 | 0.006 |
| Bacillus subtilis PCI219 | 0.025 | 0.025 |
| bacillus cereus | 0.4 | 0.4 |
| Corynebacterium dephtheriae | 0.001 | 0.001 |
| Corynebacterium xerosis | 0.001 | 0.012 |
| Mycobacterium sp. 607 | 1.56 | 1.56 |
| Mycobacterium phlei | 0.8 | 1.56 |
| Mycobacterium avium | 50.0 | 100 |
| Nocardia asteroides | 6.25 | 50.0 |
| Escherichia coli | 25.0 | 25.0 |
| Salmonella typhimurium | 100 | 100 |
| Shigella dysenteriae Shiga | 1.56 | 1.56 |
| Klebsiella pneumoniae | 1.56 | 1.56 |
| Brucella abortus | 0.8 | 1.56 |
| Serratia marcescens | 50.0 | 50.0 |
| Pseudomonas aeruginosa | 100 | 100 |
| Mucor mucedo | 100 | — |
| Saccharomyces cerevisiae | 50 | — |
| Rhodotorula glutinis | 100 | — |
| Aspergillus niger | >100 | >100 |
| Aspergillus oryzae | 100 | — |
| Pencillium glaucum | 100 | — |
| Trichophyton mentagrophytes | 50 | — |
| Candida albicans 7N | >100 | >100 |

Saframycin S exhibits an antibacterial activity mainly against gram-positive bacteria and some acidfast bacteria or gram-negative bacteria such as Mycobacterium, *Shigella dysenteriae* Shiga and Brucella. Saframycin S apparently has bioactivities almost equal to that of saframycin A.

$LD_{50}$ of saframycin S in male DDY strain mice weighing 18–20 g. is 0.83 mg/kg via intravenous injection and 2.5 mg/kg via intraperitoneal injection, respectively. The effects of saframycin S on mouse lymphoid leukemia P388 were studied with $BDF_1$ mice. When saframycin S treatment by intraperioneal injection was started 24 hours after the intraperitoneal implantation of $1 \times 10^6$ cancer cells, saframycin S at a daily dose of 0.5, 0.75, 1.0 and 1.5 mg/kg for 10 days produced, as shown in Table 5, survival period of treated group over survival period of control group of 146.2, 157.7, 161.5 and 182.7%, respectively. Said antitumor activity of saframycin S was thus proved.

TABLE 5

| Effects of saframycin S on mouse lymphoid leukemia P388 (1 × 10⁶ cells) | |
|---|---|
| dose (mg/kg/day) | increase of survival period (%) |
| 0.5 | 46.2 |
| 0.75 | 57.7 |
| 1.0 | 61.5 |
| 1.5 | 82.7 | treatment: 1-10 diseased days

Saframycin S may be employed for therapeutic purpose as an antibacterial or antitumor agent for transplantable tumors in various pharmaceutical preparation forms, such as a tablet, a powder, an oral suspension or syrup, a capsule, a solution or suspension for injection and so on. These forms may be easily prepared by the use of the antibiotic in a conventional manner. The antibiotic may be given via oral or parenteral routes, typically in intramuscular or intravenous injection. The dosage to be administered may vary under any given conditions, but in general will depend upon the severity of the disease and the age and body weight of the patient and so on. Usually, a daily dose is within a range between 10 mg and 2 g for adults and may be given in single or multiple doses.

Some embodiments of the product of the present antibiotic substance saframycin S will be shown by way of the following non-limiting examples.

EXAMPLE 1

562 mg (1 m mol) of saframycin A was added to 200 ml of 0.1 N sulfuric acid in a round-bottomed flask equipped with a Liebig condenser and heated at 120° C. of external temperature under stirring. The reaction was continued for 40 minutes capturing HCN gas produced in a 2% aqueous sodium hydroxide solution. After completion of the reaction, the reaction mixture was carefully neutralized with a saturated aqueous sodium hydrogen carbonate solution. The mixture was then extracted twice with 200 ml of ethyl acetate. The extracted was washed with water and dried over anhydrous sodium sulfate and the solvent was distilled off under reduced pressure to give 460 mg. of residue. The residue was dissolved in ethyl acetate and chromatographed over 10 g of silica gel charged in a column of 1.8×20 cm., which was then developed with benzene:ethyl acetate 2:1 under inspecting fractions with thin layer chromatography to afford 228 mg (Yield 40.5%) of the desired product.

EXAMPLE 2

562 mg (1 m mol) of saframycin A was dissolved in 30 ml of glacial acetic acid in a round-bottomed flask equipped with a Liebig condenser and followed by addition of 270 ml of water. The mixture was heated at 120° C. of external temperature under stirring. The reaction was continued for 80 minutes capturing HCN gas produced in a 2% aqueous sodium hydroxide solution. After completion of the reaction, the reaction mixture was carefully neutralized with a saturated aqueous sodium hydrogen carbonate. The mixture was then extracted twice with 200 ml of ethyl acetate. The extract was washed with water and dried over anhydrous sodium sulfate and the solvent was distilled off under reduced pressure to give 487 mg of residue. The residue was purified by column chromatography on 10 g of silica gel according to the method Example 1 to afford 102 mg (Yield 18.1%) of the desired product.

EXAMPLE 3

120 mg (0.2 m mol) of saframycin A was dissolved in 5 ml of methanol in a round-bottomed flask and followed by addition of 200 ml of a 2% $HNO_3$ solution. To the mixture was added 2 ml of a 10% aqueous $AgNO_3$ solution under stirring and ice-cooling. The mixture was left to stand overnight. The supernatant liquid was carefully neutralized with a saturated aqueous sodium hydrogen carbonate solution. The solution was then extracted twice with 100 ml of ethyl acetate. The extract was dried over an hydrous sodium sulfate and the solvent was distilled off to give 100 mg of residue, which was purified by column-chromatography on 10 g of silica gel to afford 14 mg (Yield 11.6%) of the desired product.

EXAMPLE 4

10 mg (about 0.018 m mol) of saframycin S was dissolved in 1 ml of methanol and 8 ml of 0.01 M phosphate buffer (pH 7.0) and 1 ml of 0.01 M phosphate buffer (pH 7.0) of NaCN were added successively thereto. The mixture was stirred at room temperature for 40 minutes and then extracted twice with 10 ml of ethyl acetate. The combined extract was washed with water and dried over anhydrous sodium sulfate and ethyl acetate was distilled off to give 8.2 mg of residue. The residue was dissolved in about 0.2 ml of acetone and subjected to preparative thin layer chromatography. Yellow band portions of around Rf 0.50 were collected and extracted with 10% methanol-ethyl acetate.

The extract was concentrated and treated with n-hexane to give 3.9 mg (Yield 39.8%) of yellow powder, which was identified as saframycin A by the following characteristic properties:

(1) Melting point
   122°–126° C.
(2) Elementary analysis
   C: 61.47%, H: 5.41%, N: 9.33%
(3) Molecular weight (Mass-spectrum)
   562
(4) Empirical formula
   $C_{29}H_{30}N_4O_8 \cdot 2/5H_2O$
(5) Specific rotation
   $[\alpha]_D^{20} = +18.2°$ (C=1.0, methanol)
(6) Ultraviolet absorption spectrum
   UV $\lambda_{max}^{methanol}$ nm (log ε): 267 (4.34)
   $\lambda_{min}^{methanol}$ nm (log ε): 230 (3.88)
(7) Infrared absorption spectrum
   IR $\nu_{max}^{CHCl_3}$: cm$^{-1}$: 3400, 1716, 1685, 1660, 1615
(8) NMR spectrum ($CDCl_3$)
   δ(ppm): 1.90 (3H, s), 1.98 (3H, s), 2.24 (3H, s), 2.30 (3H, s), 4.04 (6H, s), 6.65 (1H, bs).
(9) Solubility
   Easily soluble: Esters, chloroform, acetone, alcohols
   Sparingly soluble: Ethyl ether
   Insoluble: Water, n-hexane
(10) Color reaction
   Positive in Dragendorff reaction: negative in ninhydrin, perchloroiron and anthrone reactions.

EXAMPLE 5

Shaking culture in flasks

One hundred shaking flasks, each being of 500 ml-volume and containing 50 ml of the culture medium as defined below, were inoculated with the spores of *Streptomyces lavendulae* strain No. 314.

| | |
|---|---|
| Glucose | 0.5% |
| Starch | 0.5% |
| Polypepton (available from Wako Pure Chemical Industries, Ltd., Japan) | 1.0% |
| Meat extract (available from Wako Pure Chemical Industries, Ltd., Japan) | 0.5% |
| NaCl | 0.3% |
| Silicon KM-72F | 0.02% |

Cultivation was effected at 27° C. for 20 hours. After completion of the cultivation, contents of the flasks were combined and mycelia were removed by means of a continuous centrifugal separator. 4.5 l of the supernatant portion (pH 6.0) thus obtained was extracted twice each with 2 l of methylene chloride. The extracts were combined, washed with water and the solvent was distilled off under reduced pressure to give reddish brown oil. The oil was dissolved in about 100 ml of ethyl acetate and the resulting solution was washed with a saturated aqueous sodium chloride solution and then extracted three times each with 100 ml of 1 N hydrochloric acid. The combined extracts were adjusted to pH 8.0 with a conc. aqueous ammonia solution under ice-cooling and further extracted three times each with 150 ml of methylene chloride. The methylene chloride layer was washed with water and dried over anhydrous sodium sulfate and the solvent was distilled off under reduced pressure to give 620 mg of basic crude extract as a reddish brown solid. The solid was chromatographed over silica gel column (1.0×10.0 cm), which was then developed successively with ethyl acetate:benzene (1:1) and (2:1). Eluates with ethyl acetate:benzene (2:1) were collected and the solvent was distilled off to afford 62 mg of crude saframycin S as a yellow solid, which was purified by preparative thin layer chromatography (developer; benzene:ethyl acetate=1:2, Rf 0.2) to obtain 11 mg of pure saframycin S as a yellow powder.

EXAMPLE 6

Fermentation in jar fermentors

Two jar fermentors, each being of 20 l-volume and containing 12 l of the culture medium as defined below, were inoculated with the spores of *Streptomyces lavendulae* strain No. 314.

| | |
|---|---|
| Glucose | 0.5% |
| Starch | 0.5% |
| Polypepton (available from Wako Pure Chemical Industries, Ltd., Japan) | 1.0% |
| Meat extract (available from Wako Pure Chemical Industries, Ltd., Japan) | 0.5% |
| NaCl | 0.3% |
| Silicon KM-72F | 0.02% |

Cultivation was effected at 27° C. for 18 hours. After completion of the cultivation, contents of the jars were combined and about 20 l of the supernatant portion (pH 6.4) was obtained by means of a continuous centrifugal separator. The solution was extracted twice each with 10 l of methylene chloride. The extracts were combined and washed with water and then the solvent was distilled off under reduced pressure. The resulting dark red oil was dissolved in 300 ml of ethyl acetate and the solution was washed with a saturated aqueous sodium chloride solution and then extracted three times each with 150 ml of 1 N-hydrochloric acid. The combined extracts were adjusted to pH 8 with a conc. aqueous ammonia solution under ice-cooling and further extracted three times each with 300 ml of methylene chloride. The solvent layer was washed with water and dried over anhydrous sodium sulfate and the solvent was distilled off under reduced pressure to give 2.7 g of basic crude extract as a reddish brown solid. The solid was chromatographed over silica gel column (3.0×15.0 cm), which was then developed successively with ethyl acetate:benzene (1:2), (1:1) and (2:1). Eluates with ethyl acetate:benzene (1:1)–(2:1) were collected and the solvent was distilled off to afford 140 mg of crude saframycin S as a yellow solid, which was purified by preparative thin layer chromatography (developer: benzene:ethyl acetate=1:2, Rf 0.2) and then by recrystallization from a mixture of n-hexane and ether (1:1) to obtain 34 mg of pure saframycin S as a yellow powder.

What is claimed is:

1. An antibiotic substance, saframycin S, having the following physico-chemical characteristics:
color and appearance:
    dark yellow powder;
melting point:
    107°–115° C.;
specific rotation:
    $[\alpha]_D^{25} = +32.5$ (0.5 methanol);
elementary analysis:
    C: 61.09%, H: 6.67%, N: 7.49%
    C: 61.45%, H: 6.18%, N: 7.48%
molecular weight:
    553;
empirical formula:
    $C_{28}H_{30}N_3O_8^+ \cdot OH^-$
ultraviolet absorption spectrum as shown in FIG. 1:
    UV $\lambda_{max}^{MeOH}$ nm (log ε): 268 (4.21)
    UV $\lambda_{min}^{MeOH}$ nm (log ε): 234 (3.92);
infrared absorption spectrum as shown in FIG. 2:
    IR $_{max}^{CHCl_3}$ cm$^{-1}$: 3400, 1720, 1680, 1650
NMR spectrum ($C_6D_5N$) as shown in FIG. 3:
    δ: 1.88 (3H, s), 2.30 (3H, s),
    2.48 (3H, s), 2.72 (3H, s),
    3.82 (3H, s), 3.85 (3H, s),
    5.46 (1H, s).
or a pharmaceutically acceptable acid addition salt thereof.

2. A pharmaceutical composition which comprises (i) an anti-bacterially effective amount of the antibiotic substance saframycin S or acid addition salts thereof as defined in claim 1, together with (ii) a pharmaceutical carrier or excipient.

* * * * *